Figure 1:
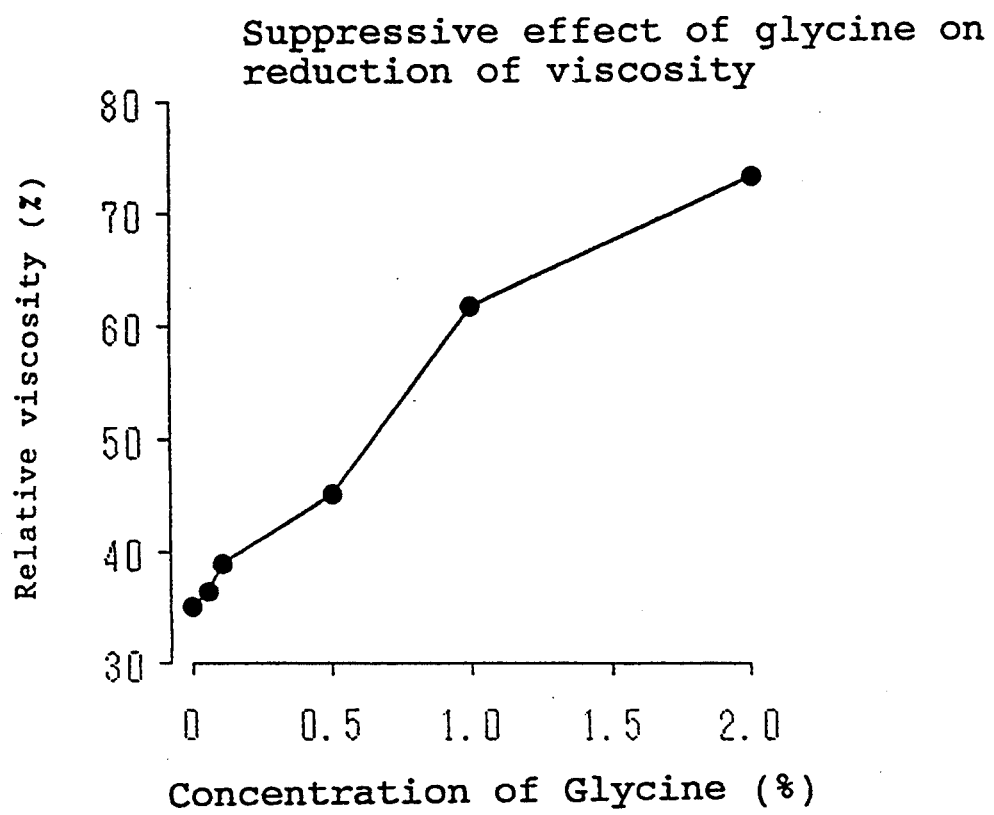

United States Patent [19]
Mitani et al.

[11] Patent Number: 5,334,378
[45] Date of Patent: Aug. 2, 1994

[54] PHARMACEUTICAL FORMULATION IN THE FORM OF AQUEOUS SUSPENSION

[75] Inventors: Youko Mitani, Suita; Kenji Muta, Shiga; Mitsuo Umemoto, Osaka, all of Japan

[73] Assignee: Rohto Pharmaceutical Co., Ltd., Japan

[21] Appl. No.: 37,360

[22] Filed: Mar. 26, 1993

[30] Foreign Application Priority Data

Apr. 2, 1992 [JP] Japan ................................. 4-081083

[51] Int. Cl.$^5$ ....................... A61K 9/08; A61K 31/74; A61K 31/95
[52] U.S. Cl. ................................. 424/78.1; 424/78.12; 521/28
[58] Field of Search ................... 521/25, 28; 424/78.1, 424/78.12

[56] References Cited

U.S. PATENT DOCUMENTS 2,697,059  12/1954  Gustus ............................. 424/78.1

FOREIGN PATENT DOCUMENTS 806M  9/1961  France .

Primary Examiner—Thurman K. Page
Assistant Examiner—Peter F. Kulkosky
Attorney, Agent, or Firm—Venable, Baetjer, Howard & Civiletti

[57] ABSTRACT

A pharmaceutical formulation in the form of aqueous suspension which comprises an ion exchange resin carrying an active ingredient and a suspending agent, characterized in that the formulation further contains a basic or neutral amino acid or a salt thereof as a dispersion stabilizer.

10 Claims, 1 Drawing Sheet

PHARMACEUTICAL FORMULATION IN THE FORM OF AQUEOUS SUSPENSION

The present invention relates to a novel pharmaceutical formulation in the form of aqueous suspension. In particular, it relates to a pharmaceutical formulation in the forth of aqueous suspension which comprises an ion exchange resin carrying an active ingredient, a suspending agent, and an amino acid as a dispersion stabilizer.

Pharmaceutical formulations in the form of aqueous suspension have been widely employed when an insoluble or hardly soluble drug must be formulated into a pharmaceutical formulation, when an active ingredient must be stabilized, when therapeutic effect of the ingredient must be prolonged, and when bitter tast of the ingredient must be masked. Since, however, the formulation in the form of aqueous suspension is a heterogenous system, it tends to undergo various detrimental changes such as exudation of water contained in polymers, which is called "syneresis", and separation or sedimentation of the dispersing particles. Such shortcomings not only give commercially undesirable appearance of the products but also have a bad influence on efficacy and safety of the products because of the fluctuation of the content of the active ingredient due to lack of uniformity of the system.

In order to solve the problems mentioned above, various attempts have been made to stabilize the system by increasing the viscosity of the system by adding suitable suspending agents (thickening agents). However, even if the system has temporarily uniformed and stabilized by such methods, the viscosity tends to decrease as the time elapses when a standard amount of the suspending agent is used (1 to 3 w/v %), and therefore, the syneresis and separation or sedimentation of particles are inevitable. When the content of the suspending agent is increased to obtain permanent stability, the product becomes too highly viscous to pour, and it becomes difficult to be measured and less palatable.

As the stabilizers for the formulation in the form of aqueous suspension, a chelating agent (Japanese Patent Publication (Kokoku) No. Sho 57-39737: Method of preparation of chocolate drinks, and Japanese Patent Publication (Kokai) No. Hei 1-240169: "condensed liquid foods") and an abisel (Japanese Patent Publication (Kokai) No. Hei 1-258618: Ibuprofen composition for children) were reported. However, satisfactory results can not be obtained when these stabilizers are used to stabilize the suspension of ion exchange resin carrying an active ingredient.

On the other hand, the use of an amino acid to stabilize a formulation in the form of aqueous suspension has already been reported (Japanese Patent Publication (Kokoku) No. Sho 63-46046), but the formulation is not the suspension comprising ion exchange particles.

It has been believed that it is quite difficult to keep the uniformity of a suspension for a prolonged period, where the suspension comprises relatively large particles (1 to 500 μm) such as ion exchange resins dispersed in an aqueous medium. Accordingly, it has been believed that there is no means other than trying to maintain resuspendability in order to achieve a uniform suspension again by shaking when the particles have separated or sedimented, as stated in Japanese Patent Publication (Kokoku) No. Sho 63-46046 mentioned above.

Now it has been found that, in a case of a pharmaceutical formulation in the form of aqueous suspension containing such particles that have relatively greater specific gravity and larger particle size, such as an ion exchange resin carrying an active ingredient, a stable formulation capable of maintaining a uniform dispersion for a prolonged period can be obtained by adding a suspending agent (thickening agent) to increase the viscosity which allows uniform dispersion, and then adding an amino acid as a dispersion stabilizer.

Thus, an objective of the present invention is to provide a pharmaceutical formulation in the form of aqueous suspension which comprises an ion exchange resin carrying an active ingredient and a suspending agent, characterized in that the formulation further contains a neutral or basic amino acid or a salt thereof as a dispersion stabilizer.

In the present invention, the nature of an active ingredient is not critical except that it is an agent capable of being converted to an ion. Specific examples of the active ingredient include codeine, dihydrocodeine, dexstromethorphan, chlorpheniramine, phenylpropanolamine, methylephedrine and hydrocodone and the like.

In this text, the ion exchange resin carrying an active ingredient means a complex of an active ingredient and an ion exchange resin selected from a wide range of resins. For the purpose of extending the biological half life of an active ingredient, the ion exchange resin complex may be further admixed with a solvating agent, followed by coating with a polymer such as ethylcellulose to form a diffusion barrier material, and such complex is also within the meaning of the ion exchange resin carrying an active ingredient in the present invention. Average particle size of the ion exchange resin complex is preferably within the range from 1 to 500 μm, most preferably from 25 to 250 μm. The amount of the complex to be dispersed is preferably 3 w/v % or less based on the total amount of the suspension formulation. When both of the average particle size and the amount of the complex to be dispersed are small, then the uniform dispersion can be established easily. On the other hand, when the particle size is 500 μm or more and the amount of the complex to be dispersed is 3 w/v % or more, then additional countermeasures such as increasing viscosity or specific gravity may be required.

The suspending agent used in the present invention may be, for example, natural gums such as tragacanth gum and xanthane gum, nonionic cellulose derivatives such as methylcellulose, hydroxyethylcellulose, hydroxypropylcellulose and hydroxypropylmethylcellulose as well as propylene glycol alginate and mixture thereof. The combination of tragacanth gum and xanthane gum is preferred. The amount of the suspending agent to be incorporated ranges preferably from 0.1 to 3 w/v %, most preferably from 0.5 to 1.5 w/v %, so as to establish the viscosity of about 1300 cps (Type B viscometer, 25° C.). Maintenance of uniformity may become difficult when the amount of the suspending agent is smaller than the above lower limit. On the other hand, when the amount of the suspending agent is higher than the upper limit, then the formulation may not be weighed correctly, and the final product may have the efficacy/safety problems and may be less palatable, which brings undesirable results in the market.

The dispersion stabilizer used in the present invention may be, for example, a neutral amino acid such as glycine, alanine, valine and cysteine and a basic amino acid such as lysine, histidine and arginine as well as the salts thereof.

As shown in the working Examples, marked reduction in viscosity is observed as the time elapses when the viscosity of the system has been increased without adding an amino acid, while the reduction in viscosity can be retarded in the system containing an amino acid described above. This effect of retardation is dose-dependent, and the amount of an amino acid mentioned above is preferably from 0.05 to 2 w/v %. When the amino acid is added in an amount of 1% or higher, almost no reduction in viscosity occurs and sufficient effect can be obtained. On the other hand, when the amino acid is added at an excessively high concentration, the amino acid itself may act as a zwitterion compound and adversely effect the interaction between the ion exchange resin and the active ingredient and brings an undesirable effect.

In the present invention, the stability of the aqueous suspension can be further enhanced by adding a polyhydric alcohol. Such polyhydric alcohol may be, for example, propylene glycol, glycerin, sucrose, sorbitol and the like. Propylene glycol and sorbitol are most preferred. It is also useful for stabilization of the suspension to add a vegetable syrup (isomerized sugar) to increase the specific gravity.

The pharmaceutical formulation in the form of aqueous suspension according to the present invention may also contain, as necessary, preservatives, stabilizers, pH modifiers, flavoring agents and the like.

The method of stabilizing the pharmaceutical formulation according to the present invention can be applied to weakly-acidic or neutral suspensions having the pH of from 3 to 7.

FIG. 1 of the accompanying drawing shows the reduction of viscosity of pharmaceutical formulations in the form of aqueous suspension after storage for 8 months at room temperature, which contain glycine at various concentrations.

The present invention is further described in the following working Examples, which are not intended to restrict the scope of the invention in any way.

EXAMPLE 1

(1) Preparation of coated (codeine)-(ion exchange resin) complex particles

Coated (codeine)-(ion exchange resin) complex particles having the coating ratio of about 11% were obtained as follows using polyethylene glycol as a solvating agent and ethylcellulose as a diffusion barrier material.

A. Preparation of (codeine)-(ion exchange resin) complex 95.0 g of codeine phosphate was dissolved in 950 ml of deionized water. While stirring, 359.9 g of Amberlite ® IRP-69 was added thereto and the mixture was stirred for 1 hour. The resultant (codein)-(ion exchange resin) complex was collected on a buchner funnel and washed thoroughly, and then dried in a fluidized bed drier at an inlet air temperature of 60° C. for 1 hour to yield (codeine)-(ion exchange resin) complex.

B. Preparation of polyethylene glycol-treated resin complex

To 350 g of the (codeine)-(ion exchange resin) complex obtained above, 82.5 g of polyethylene glycol 4000 dissolved in 104.8 ml of deionized water was dropwise added with stirring. After further mixing for 15 minutes, the mixture was dried in the fluidized bed drier for 1 hour at an inlet air temperature of 40° C. to yield polyethylene glycol-treated (codeine)-(ion exchange resin) complex.

C. Preparation of a coating solution 45.0 g of ethylcellulose and 21.2 g of Durkex ® 500 were dissolved in a mixture of 130.4 g of acetone and 1304.0 g of methylene chloride.

D. Preparation of coated (codeine)-(ion exchange resin) complex

Using a Wurster type coater, the coating solution was sprayed at the rate of 8 g/min onto 400 g of polyethylene glycol-treated (codeine)-(ion exchange resin) complex at an inlet air temperature of 40° C. so that the amount of the coating was 11.0 w/v % based on the complex (total amount 998 g).

(2) Preparation of (chlorpheniramine)-(ion exchange resin) complex particles 86.0 g of chlorpheniramine maleate was dissolved in 1634.0 ml of deionized water. While stirring, 200.0 g of Amberlite ® IRP-69 was added thereto and the mixture was stirred for 30 minutes. The resultant complex was collected on a buchner funnel and washed thoroughly, and then dried in a fluidized bed drier at an inlet air temperature of 60° C. for 1 hour to yield (chlorpheniramine)-(ion exchange resin) complex.

(3) Preparation of a pharmaceutical formulation in the form of aqueous suspension A natural gum such as tragacanth gum or xanthane gum was dispersed in a polyhydric alcohol such as propylene glycol, and a preservative such as paraben was added if necessary to form a slurry. The slurry was portion wise added to an aqueous solution of a syrup, saccharides and an amino acid, for example, a neutral amino acid such as glycine, alanine, valine and cysteine, or a basic amino acid such as lysine, histidine and arginine and the salts thereof, and the mixture was stirred thoroughly to establish a uniform dispersion. The mixture of coated (codeine)-(ion exchange resin) complex particle and (chlorpheniramine)-(ion exchange resin) complex particles which had been hydrated previously with a small amount of deionized water containing a surfactant was added thereto and the concentration of the particles was adjusted with an appropriate amount of water to obtain each of the pharmaceutical formulations in the form of aqueous suspension shown in Table 1 and Table 2. The formulations Rp-9 and Rp-11 in the table were adjusted to about pH 4.0 with hydrochloric acid or sodium hydroxide.

TABLE 1

| Components | Rp-1 | Rp-2 | Rp-3 | Rp-4 | Rp-5 | (w/v %) Rp-6 |
|---|---|---|---|---|---|---|
| Coated codeine-resin complex | 1.57 | 1.57 | 1.57 | 1.57 | 1.57 | 1.57 |
| Chlorpheniramine-resin complex | 0.18 | 0.18 | 0.18 | 0.18 | 0.18 | 0.18 |
| Glycine | — | 1.0 | — | 1.0 | — | 1.0 |
| Tragacanth gum | 0.9 | 0.9 | — | — | 0.675 | 0.675 |
| Xanthan gum | — | — | 0.7 | 0.7 | 0.18 | 0.18 |
| Propylene glycol | 1.0 | 1.0 | 1.0 | 1.0 | 1.0 | 1.0 |
| Methylparaben | 0.15 | 0.15 | 0.15 | 0.15 | 0.15 | 0.15 |

TABLE 1-continued

| Components | Rp-1 | Rp-2 | Rp-3 | Rp-4 | Rp-5 | Rp-6 (w/v %) |
|---|---|---|---|---|---|---|
| Propylparaben | 0.03 | 0.03 | 0.03 | 0.03 | 0.03 | 0.03 |
| Corn syrup | 30 | 30 | 30 | 30 | 30 | 30 |
| Citric acid | 0.1 | 0.1 | 0.1 | 0.1 | 0.1 | 0.1 |
| Purified water | q.l. | q.l. | q.l. | q.l. | q.l. | q.l. |
| Total | 100 | 100 | 100 | 100 | 100 | 100 |
| Syneresis* | +++ | ± | ± | − | +++ | ± |
| Sedimentation* | +++ | ± | +++ | − | +++ | ± |

*After storange for 6 months at room temperature

TABLE 2

| components | Rp-7 | Rp-8 | Rp-9 | Rp-10 | Rp-11 | Rp-12 (w/v %) |
|---|---|---|---|---|---|---|
| Coated codeine-resin complex | 1.57 | 1.57 | 1.57 | 1.57 | 1.57 | 1.57 |
| Chlorpheniramine-resin complex | 0.18 | 0.18 | 0.18 | 0.18 | 0.18 | 0.18 |
| Alanine | 1.0 | — | — | — | — | — |
| Valine | — | 1.0 | — | — | — | — |
| Cysteine hydrochloride (monohydrate) | — | — | 1.45 | — | — | — |
| Lysine hydrochloride | — | — | — | 1.25 | — | — |
| Arginine | — | — | — | — | 1.0 | — |
| Histidine hydrochloride (monohydrate) | — | — | — | — | — | 1.35 |
| Tragacanth gum | 0.675 | 0.675 | 0.675 | 0.675 | 0.675 | 0.675 |
| Xanthan gum | 0.18 | 0.18 | 0.18 | 0.18 | 0.18 | 0.18 |
| Propylene glycol | 1.0 | 1.0 | 1.0 | 1.0 | 1.0 | 1.0 |
| Methylparaben | 0.15 | 0.15 | 0.15 | 0.15 | 0.15 | 0.15 |
| Propylparaben | 0.03 | 0.03 | 0.03 | 0.03 | 0.03 | 0.03 |
| Corn syrup | 30 | 30 | 30 | 30 | 30 | 30 |
| Citric acid | 0.1 | 0.1 | 0.1 | 0.1 | 0.1 | 0.1 |
| Hydrochloric acid | — | — | — | — | q.l. | — |
| Sodium hydroxide | — | — | q.l. | — | — | — |
| Purified water | q.l. | q.l. | q.l. | q.l. | q.l. | q.l. |
| Total | 100 | 100 | 100 | 100 | 100 | 100 |
| Syneresis* | ± | ± | ± | − | − | − |
| Sedimentation* | ± | ± | ± | − | − | − |

*After storage for 6 months at room temperature (4) Evaluation

Twelve formulations listed above were allowed to stand at room temperature for 6 months, and the stability of dispersed condition of the formulations was evaluated using syneresis and sedimentation of dispersed particles as indices. As a result, it was found that almost all formulations containing amino acids did not develop syneresis and sedimentation. Even when developed, degree of the syneresis and sedimentation was far less than that of the formulations containing no amino acids. Accordingly, it was evident that the amino acids contributed significantly to the stabilization of the dispersed condition of the formulations.

The mechanism by which the amino acids prevent the suspension from developing syneresis and sedimentation was examined. Thus, by using Rp-5 as a standard formulation and adding glycine in an amount within the range of from 0.05 to 2 w/v % to form a suspension, the influence of the addition of amino acid on reduction of viscosity was examined.

The viscosity of each of the formulations containing glycine at various concentrations, which were stored at room temperature for about 8 months, was measured and compared with the initial viscosity (FIG. 1). The results indicated that glycine suppressed the reduction of viscosity of the suspension in a dose-dependent manner within the range of the concentration of 0.05 w/v % or higher.

Accordingly, it is believed that an amino acid suppresses the reduction of viscosity by means of strengthening 2- or 3-dimensional structure of the molecules in a dispersed solution of natural gums such as tragacanth gum and xanthane gum, nonionic cellulose derivatives such as methylcellulose, hydroxyethylcellulose, hydroxypropylcellulose and hydroxypropylmethylcellulose, and synthetic polymers such as propyleneglycol arginate.

What is claimed is:

1. A pharmaceutical formulation in the form of an aqueous suspension capable of maintaining a uniform dispersion upon storage which comprises (a) 0.01-3.00 w/v % of an ion exchange resin carrying an active ingredient capable of being converted into an ionic active ingredient, (b) 0.10-3.00 w/v % of a suspending agent selected from the group consisting of natural gums, nonionic cellulose derivatives and alginates and mixtures thereof, (c) 0.05-2.00 w/v % of a dispersion stabilizer comprising an amino acid selected from the group consisting of glycine, alanine, cystine, valine, lysine, arginine, histidine and salts thereof and (d) 92.00-99.84 w/v % of water, wherein said maintained uniform dispersion is the effect of the amino acid dispersion stabilizer on the ion exchange resin carrying an active ingredient and the suspending agent.

2. A pharmaceutical formulation of claim 1, wherein the suspending agent is one or more natural-gums.

3. A pharmaceutical formulation of claim 1, wherein the suspending agent is selected from non-ionic cellulose derivatives consisting of methylcellulose, hydroxyethylcellulose, hydroxypropylcellulose, and hydroxypropylmethylcellulose.

4. A pharmaceutical formulation of claim 1, wherein the concentration of the suspending agent is 0.5 to 1.5 w/v % with respect to the total volume of the formulation.

5. A pharmaceutical formulation of claim 1, wherein the concentration of the amino acid or its salt is 1.0 to 2 w/v % with respect to the total volume of the formulation.

6. A pharmaceutical formulation of claim 1, wherein the average particle size of the ion exchange resin carrying the active ingredient is 1 to 500 μm in a dried state.

7. A pharmaceutical formulation of claim 1, which is weakly acidic or neutral and shows pH 3 to 7.

8. The pharmaceutical formulation of claim 6 wherein the average particle size is 25 to 250 μm.

9. The pharmaceutical formulation of claim 1 wherein said active ingredient is selected from the group consisting of codeine, dihydrocodeine, dexstromethorphon, chlorpheniramine, phenylpropanolamine, methylephedrine and hydrocodone.

10. The pharmaceutical formulation of claim 1 wherein the suspending agent is a combination of tragacanth gum and xanthane gum.

* * * * *